(12) United States Patent
Mao et al.

(10) Patent No.: US 6,960,169 B2
(45) Date of Patent: Nov. 1, 2005

(54) SPREAD SPECTRUM CODING FOR ULTRASOUND CONTRAST AGENT IMAGING

(75) Inventors: Zuhua Mao, Issaquah, WA (US); Hui Jiang, Issaquah, WA (US); Patrick Von Behren, Bellevue, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 94 days.

(21) Appl. No.: 10/441,325

(22) Filed: May 19, 2003

(65) Prior Publication Data

US 2004/0236222 A1 Nov. 25, 2004

(51) Int. Cl.[7] ............................................. A61B 8/14
(52) U.S. Cl. ..................................................... 600/458
(58) Field of Search .............................. 600/437, 443, 600/447–458; 424/9.51, 9.52; 128/916

(56) References Cited

U.S. PATENT DOCUMENTS

| | | | |
|---|---|---|---|
| 5,410,516 A | | 4/1995 | Uhlendorf et al. |
| 5,577,505 A | | 11/1996 | Brock-Fisher et al. |
| 5,601,086 A | | 2/1997 | Pretlow, III et al. |
| 5,608,690 A | | 3/1997 | Hossack et al. |
| 5,632,277 A | | 5/1997 | Chapman et al. |
| 5,675,554 A | | 10/1997 | Cole et al. |
| 5,678,553 A | | 10/1997 | Uhlendorf et al. |
| 5,706,819 A | | 1/1998 | Hwang et al. |
| 5,935,070 A | * | 8/1999 | Dolazza et al. .............. 600/443 |
| 5,951,478 A | | 9/1999 | Hwang et al. |
| 6,034,922 A | | 3/2000 | Uhlendorf et al. |
| 6,064,628 A | | 5/2000 | Uhlendorf et al. |
| 6,095,980 A | | 8/2000 | Burns et al. |
| 6,193,663 B1 | | 2/2001 | Napolitano et al. |
| 6,213,947 B1 | | 4/2001 | Phillips |
| 6,221,899 B1 | | 4/2001 | Nishida et al. |
| 6,241,674 B1 | | 6/2001 | Phillips et al. |
| 6,371,917 B1 | | 4/2002 | Ferrara et al. |
| 6,440,074 B1 | * | 8/2002 | Averkiou ..................... 600/443 |
| 6,440,075 B1 | * | 8/2002 | Averkiou ..................... 600/443 |
| 6,443,899 B2 | | 9/2002 | Uhlendorf et al. |
| 6,494,839 B1 | * | 12/2002 | Averkiou ..................... 600/443 |

OTHER PUBLICATIONS

"Higher Order Nonlinear Ultrasonic Imaging," by Brune Haider and Richard Y. Chiao; 1999 IEEE Ultrasonics Symposium; pp. 1527–1531.

"Bubble Size Measurements Using the Nonlinear Mixing of Two Frequencies," by V.L. Newhouse and P. Hohana Shankar; 1984 Acoustical Society of America; pp. 1473–1477.

* cited by examiner

Primary Examiner—Ali Imam

(57) ABSTRACT

Contrast agent imaging uses spread spectrum coding. The contrast-to-tissue ratio and signal-to-noise ratio for contrast agent imaging is improved by transmitting a waveform with pulses at two or more frequencies. In one embodiment, signals received at an intermodulation frequency responsive to the two transmitted frequencies are isolated and used for imaging. As a result of the differences in responses of contrast agent and tissue to the frequency transitions between pulses, information from contrast agent with minimal influence from tissue is identified. In another embodiment, two waveforms with pulses at two or more frequencies are sequentially transmitted.

23 Claims, 3 Drawing Sheets

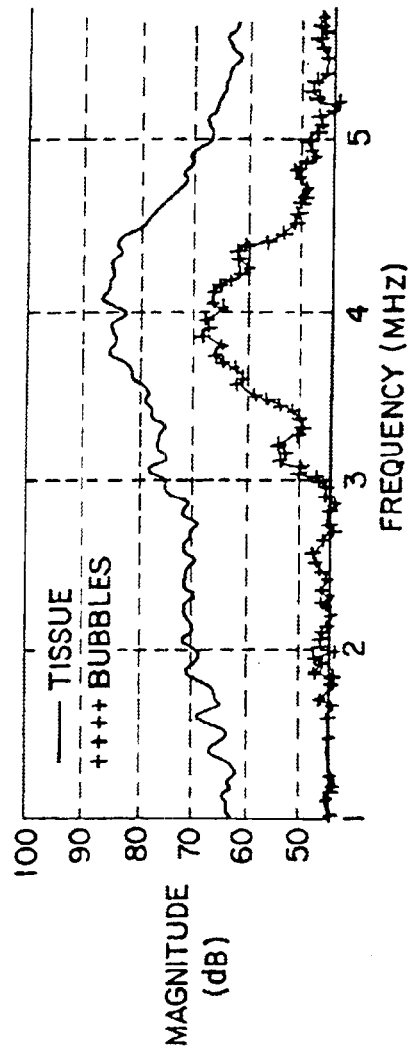
FIG.4A
FIG.4B
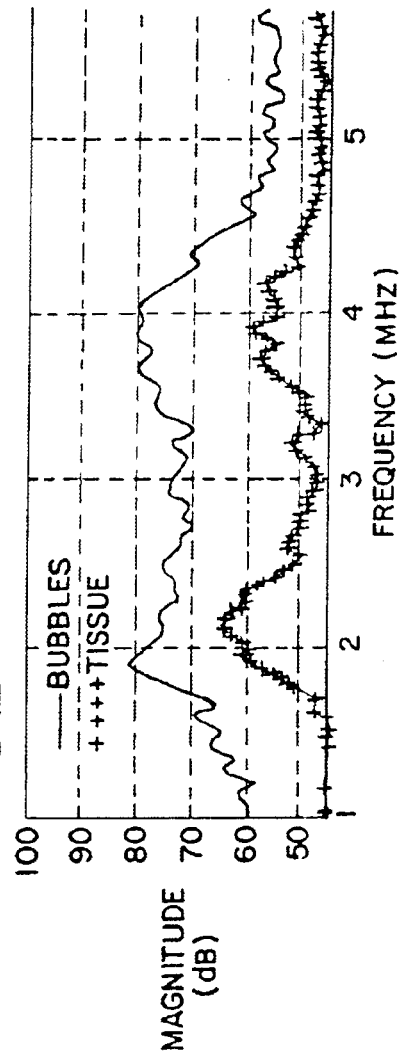
FIG.5A
FIG.5B

SPREAD SPECTRUM CODING FOR ULTRASOUND CONTRAST AGENT IMAGING

BACKGROUND

This present invention relates to contrast agent imaging. In particular, transmission techniques for ultrasound contrast agent imaging are provided.

Contrast agents are injected into a patient's tissue. Due to a difference in response between contrast agents and fluids or contrast agents and tissues, contrast agents may assist diagnosis, such as for the assessment and differentiation of viable myocardium from nonviable myocardium, detection and characterization of focal liver lesions, indeterminate renal lesion characterization, breast lesion characterization, transcraneal studies, early identification of prostate lesions, or other vascular visualization enhancements. Being able to separate contrast agents from tissue in ultrasound imaging may assist diagnosis. However, contrast agents are destroyed by high power ultrasound, and tissue and contrast agents may have similar responses at fundamental frequencies of lower power transmitted ultrasound.

Various techniques have been developed for low mechanical index or low energy ultrasound contrast agent imaging. In one approach, the difference in harmonic response of contrast agents from tissues provides better contrast to tissue ratio. Two or more waveforms are transmitted sequentially with different phases, such as opposite phasing. By adding the responses to each of the sequential transmissions, acoustic energy at fundamental frequencies is cancelled out and second harmonic energy remains. However, tissue does generate some second harmonic or other harmonic information, reducing the desired contrast tissue ratio. Various other techniques for transmitting two or more pulses sequentially with different phases and/or magnitudes and then combining responsive echoes with different weightings and with different functions to cancel tissue signals and detect contrast agents has been suggested. In order to achieve better suppression of tissue signals, echoes responsive to three or more sequential transmissions are combined, but at a sacrifice of frame rate.

BRIEF SUMMARY

The present invention is defined by the following claims, and nothing in this section should be taken as a limitation on those claims. By way of introduction, the preferred embodiments described below include methods and systems for spread spectrum coding and ultrasound contrast agent imaging. The contrast-to-tissue ratio and signal-to-noise ratio for contrast agent imaging is improved by transmitting a waveform with pulses at two or more frequencies. In one embodiment, signals received at an intermodulation frequency responsive to the two transmitted frequencies are isolated and used for imaging. As a result of the differences in responses of contrast agent and tissue to the frequency transitions between pulses, information from contrast agent with minimal influence from tissue is identified. In another embodiment, two waveforms with pulses at two or more frequencies are sequentially transmitted.

In a first aspect, a method for spread spectrum coding and ultrasound contrast agent imaging is provided. A first waveform having pulses at first and second frequencies is transmitted. The first frequency is different than a second frequency. Information responsive to the transmission is isolated at an intermodulation frequency. An image responsive to the isolated information is generated.

In a second aspect, an improvement in a method for ultrasound contrast agent imaging is provided. Ultrasound energy is transmitted into a region with tissue and contrast agent. Echoes of the energy from the tissue and contrast agent are received. The transmission is improved by transmitting at least two waveforms sequentially into the region. Each of the two waveforms has pulses at two or more different frequencies. The pulses are cascaded with a step transition between the frequencies.

Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 4A is a graphical representation of a transmit waveform of a single frequency band in one embodiment, and FIG. 4B is the response of tissue and contrast agent to the waveform of FIG. 4A;

FIG. 5A is a graphical representation of one embodiment of a transmit waveform with pulses at two different frequencies, and FIG. 5B is a graphical representation of the response of tissue and contrast agents to the waveform of FIG. 5A.

DETAILED DESCRIPTION OF THE DRAWINGS AND PRESENTLY PREFERRED EMBODIMENTS

To provide good contrast-to-tissue ratio and signal-to-noise ratio information, contrast agent information is isolated or separable from tissue signal information. Tissue signals are suppressed while keeping information responsive to contrast agents. Using low mechanical index or low amplitude transmit waveforms, a limited amount of tissue harmonic information and substantial contrast agent harmonic information are generated. By insonnifying the contrast agent at the resonant frequency, a relative high contrast agent response for both the fundamental and harmonics is provided as opposed to tissue information.

To further maximize the contrast-to-tissue ratio, pulses responsible at two different frequency bands are transmitted as a waveform where the pulses are closely spaced in time, such as cascading pulses at a first frequency after pulses of a second frequency. This separation of the pulses of different frequencies is kept to a minimal amount of time, such as several microseconds or less. The tissue response to sudden changes in frequency is different or less than the contrast agent response. As a result, intermodulation frequencies responsive to the two transmitted frequency bands include contrast information with minimal tissue information. These multi-band non-linear components and loss of correlation information are detected in response to a minimal number of transmit pulses, maintaining a good frame rate. Using additional transmissions, such as three or more firings may allow isolating information at higher order harmonics.

Figure 1:
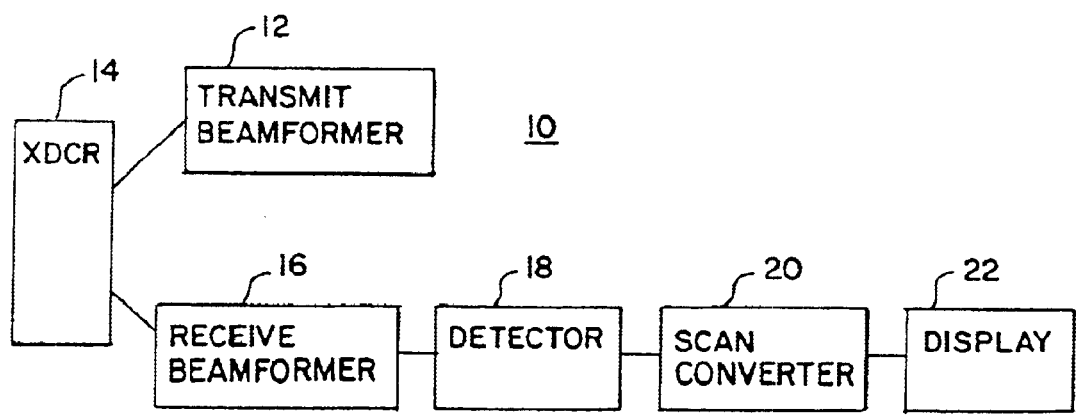
FIG. 1 is a block diagram of one embodiment of a system for ultrasound contrast agent imaging.

By providing pulses at two different frequency bands, spread spectrum coding is provided for ultrasound contrast agent imaging. FIG. 1 shows an ultrasound system 10 for spread spectrum coding and ultrasound contrast agent imaging. The system 10 includes a transmit beamformer 12, a transducer 14, a receive beamformer 16, a detector 18, a scan converter 20 and a display 22. Different, additional or fewer components may be provided. In one embodiment, the system 10 is one of the Elegra, Antares, Aztec, Sequoia® or Aspen ultrasound systems for medical diagnostic imaging from Siemens Medical Solutions USA Inc. In alternative embodiments, ultrasound systems from other manufacturers are used.

The transmit beamformer 12 comprises one or more channels for generating a waveform, such as a waveform memories, delays, amplifiers, waveform generators, pulsers, oscillators, and/or digital to analog converters. Waveform generators that produce unipolar, bipolar or complex waveforms may be used. Using start of transmission or delay controls, the transmit beamformer 12 is operable to generate unipolar, bipolar or sinusoidal waveforms with pulses at two different frequencies (e.g. different pulse widths) during a given transmission. By either designating an arbitrary waveform, by adjusting delays or the start signal, sequential pulses associated with different frequency bands are generated by the transmit beamformer 12. Using a uniform or bipolar transmit waveform generator, cascaded pulses are stored in a memory for generating a pulse width modulated or pulses of different frequency bands during a single firing. For an arbitrary or programmable waveform generator, two or more signals are used to generate the optimal waveforms with relative delays within a channel. The two waveforms are combined to generate the waveforms discussed herein. Alternatively, amplitude, phase and other information is stored to arbitrarily generate a single waveform with the pulses at different frequencies. In one embodiment, a linear amplifier or structure is disclosed in U.S. Pat. No. 5,675,554, the disclosure of which is incorporated herein by reference, is used.

In one embodiment, each channel is operable to generate the waveform described herein. In alternative embodiments, two or more channels generate different portions of a waveform that are combined prior to transduction, combined at the transducer, or combined in the acoustic domain. For example, pulses at one frequency band are generated by a first channel or waveform generator and pulses at a different frequency band are generated by a different channel or waveform generator. The separate pulses are then combined as a single waveform applied to a region under examination for a single firing.

The transducer 14 comprises one or more piezoelectric for microelectromechanical transducer elements. A transducer 14 receives waveforms generated by the transmit beamformer 12 and converts the electrical waveforms into acoustic waveforms. The acoustic waveforms are transmitted along one or more scan lines for each single burst of transmitted energy from one or more elements. Relative delays between the transmitted acoustic energy of a plurality of elements allow focusing the ultrasound energy along the scan line or at a point. The region of the patient that is insonnified may include tissue, contrast agent or both tissue and contrast agent. In response to the transmit waveforms, echo signals are generated by the tissue or contrast agent. Some echo signals are reflected back to the transducer 14. The transducer 14 converts the received echoes into electrical signals.

The receive beamformer 16 receives the electrical signals from the transducer 14. The receive beamformer 16 is any one of now known or later developed receive beamformers for converting electrical signals from multiple elements into signals representative of spatial locations along one or more scan lines.

The detector 18 receives the signals representing spatial locations within the patient. The detector 18 detects a characteristic of the signals. For example, the detector 18 is a B-mode detector, a Doppler velocity, energy or variance detector, an M-mode detector or a spectral Doppler detector. In one embodiment, the detector 18 comprises any one or more of the structures disclosed in U.S. Pat. Nos. 5,632,277, 5,706,819, 5,951,478, 6,095,980, 6,193,663, 6,213,947, 6,241,676, 5,577,505, and 6,949,841 the disclosures of which are incorporated herein by reference. The above cited patents disclosed various detectors for detecting contrast agents in response to two or more pulses. For example, intensities responsive to the same transmit waveforms transmitted sequentially 180 degrees out of phase are added together (i.e. pulse inversion) to cancel information at odd harmonics while maintaining information at even harmonics. The intensity of the isolated information is detected. Pulse inversion may be used for Doppler imaging techniques or by transmitting pulse inverted waveforms from different elements at a same time to avoid multiple transmissions. Alternatively, any differences or a loss of correlation between multiple receive signals is detected. Different modulation, coding, or relative amplitudes may be used within transmit waveforms to identify or detect intensity, velocity, loss of correlation, acceleration or other information associated with contrast agent at one or more frequency bands. Any detectors now known or later developed for contrast agent imaging may be used.

The scan converter 20 receives detected information and reformats from the polar coordinate system to a Cartesian or display coordinate system. The display 22 displays the resulting image.

Figure 2:
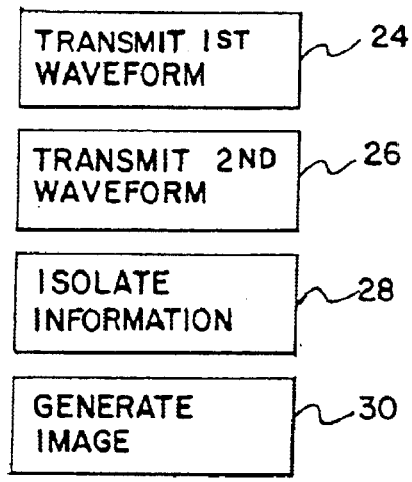
FIG. 2 is a flow chart diagram of one embodiment of a method for contrast agent imaging.

FIG. 2 shows a method for spread spectrum coding and ultrasound contrast agent imaging. The method includes transmitting first and second waveforms 24, 26 sequentially or in different firings. In act 28, information responsive to the waveforms is isolated. An image is generated from the isolated information in act 30. Different, additional or fewer acts may be provided, such as transmitting a first waveform without transmitting a second waveform or transmitting more than two waveforms sequentially to generate the isolated information. In one embodiment, any of the various multi-pulse contrast agent imaging methods described in the patents noted above, now known or later developed is used, such as pulse or phase inversion or contrast pulse sequences. For pulse inversion, at least two waveforms are sequentially transmitted into a same region (e.g., along the same or adjacent scan lines). One or each of the waveforms has different pulses at different frequencies, such as pulses at one frequency cascaded sequentially after pulses at a different frequency.

Figure 3:
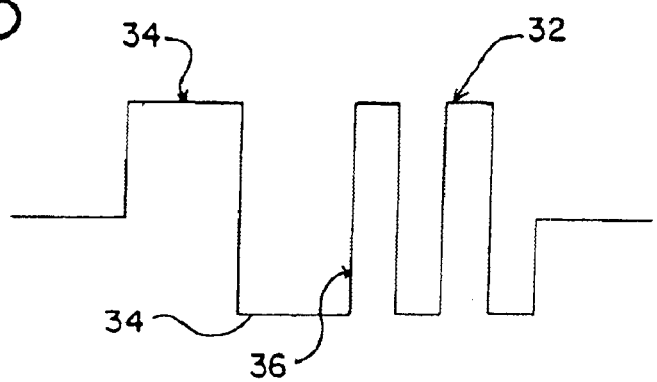
FIG. 3 is a graphical representation of a transmit waveform with pulses at two different frequencies of one embodiment.

In act 24, a waveform having pulses at two different frequencies is transmitted. Pulses at three or more different frequencies may be used. FIG. 3 shows one example of pulses at two different frequencies cascaded with a step transition between the frequencies. A single cycle bipolar waveform with a positive and a negative pulse 34 at a first frequency is cascaded with the two cycle waveform with pulses 32 at a second frequency. The transition 36 from the pulses 34 to the pulses 32 are cascaded with no delay. The pulses 34 and 32 are sequential without any overlap. A further delay may be provided between the pulses 34 and the pulses 32 at any of various amplitude levels, possibly resulting in a pulse at a different frequency. The transition 36 is associated with a step in frequencies. For example, a difference between the frequencies of the two different pulses is greater than half of the least of the frequencies. For example, pulses 34 are at 1.25 or 2 MHz and the pulses 32 are at 3.75 or 4 MHz, respectively. The difference in frequencies is 2.75 and 2 respectively. Different frequencies may be used. By providing a step transition between frequencies, a greater intermodulation response is provided by the contrast agents. A step transition is a transition between frequencies sufficient to generate a different intermodulation response of contrast agents than tissue. As shown in FIG. 3, pulses at only two primary frequencies are used for a given waveform, but pulses at three or more primary frequencies may be provided.

As shown in FIG. 3, low frequency pulses 34 precede the cascaded high frequency pulses 32. In alternative embodiments, the high frequency pulses 32 precede the cascaded low frequency pulses 34. In yet other alternative embodiments, pulses at one frequency are sandwiched between pulses of one or more different frequency bands.

The waveform of FIG. 3 or another waveform generated in act 24 is transmitted from a plurality of elements of the transducer 14 substantially simultaneously. Substantially is used to account for inaccuracies in waveform generation as well as intentional delays for focusing. Pulses at both of the two different frequencies are transmitted from a plurality of elements in a single firing. In one embodiment, the pulses at each of the different frequencies are focused at a same focal point or region. In alternative embodiments, different amplitude or phasing (i.e. delays) of pulses at one frequency is provided than for pulses at a different frequency. For example, pulses at one frequency are focused at a different focal point than pulses at a different frequency in the same waveform or firing. As a result and depending on a location within the transmit aperture, a different amount of delay of the transition 36 between pulses is provided. By managing the transmit aperture, such as the aperture size, apodization shape, transmit focus and relative gain of the pulses at the different frequencies independently, a more uniform energy distribution is provided with depth and angle of scan line. Independent control may allow for different frequencies to be used for a given transducer frequency response and tissue attenuation.

In one example, the acoustic energy is more evenly distributed along a scan line by setting different amplitudes and/or phasings or other aperture characteristics of one frequency pulse as compared to another frequency pulse. The cascaded waveform shown in FIG. 3 or described above is transmitted from a center of the transmit aperture, but pulses at only one of the frequencies or a different singular frequency band are transmitted at the edges of the transmit aperture. The ratio of the center aperture to the total aperture width determines the energy ratio of the two frequency components. The aperture width for transmitting the single frequency pulse may also be used as an independent parameter to further adjust the energy ratio of the two different frequency components. The number of cycles or links of the single frequency pulse is shorter than, longer than, or a same length as the cascaded waveform applied to the center of the aperture.

As another example, pulses at different frequencies are focused to different depths to account for different attenuation characteristics of a given frequency. As a result, an axis uniformity of the energy ratio along a scan line (i.e. line focus) may be provided. For example, the frequency dependent focusing disclosed in U.S. Pat. No. 5,608,690 is used, the disclosure of which is incorporated herein by reference. Where a multiple dimensional array, such as 1.5 or two-dimensional array is provided, characteristics of the different pulses are determined independently as a function of the elevation aperture to provide better on-axis uniformity of the acoustic energy along the scan line. Such on-axis uniformity provides a line or a region focus for more uniform or even response.

In addition to on-axis uniformity, characteristics of pulses at one frequency may differ independently of characteristics of pulses at a different frequency for reducing grading lobes. By restricting the aperture size for pulses at one frequency, such as the higher frequency, grading lobes may be minimized. In another embodiment, the relative gain between pulses at different frequencies is adjusted, such as by setting a different amplitude. As an alternative, the gain is adjusted by modulating the width of the pulses at a given frequency band. For example, bipolar or unipolar pulses with modulated width may be used to reduce or shape the energy response of the pulses. By adjusting the relative gain, the different frequencies may be optimized to generate an intermodulation frequency at the resonant frequency of a given contrast agent.

In one embodiment, the frequencies of the pulses 32, 34 are selected as a function of the contrast agent resonant frequency. For example, the resonant frequency is given as $F_0$ and is a function of the particular contrast agent. The low frequency is selected as half of the resonant frequency and the high frequency is selected as 1.5 times the resonant frequency for low frequency applications. For example, a 3.5 MHz transducer 14 used for imaging contrast agents with a resonant frequency of 2.5 MHz transmits a waveform with pulses at 1.25 and 3.75 MHz. Using a different transducer 14 and a different contrast agent with the resonant frequency of 2 MHz, a higher frequency application may be used, such as transmitting a waveform with pulses at 2 MHz and 4 MHz. Any of various combinations with different frequencies above, below, or both above and below the resonant frequency may be used. In one embodiment, the low frequency is selected as one-half or equal to the resonant frequency and the higher frequency is selected such that the higher frequency minus the lower frequency equals the resonant frequency. Where the lowest frequency is half the resonant frequency, the second and third harmonics generated by the low frequency pulses and the second order intermodulation component (e.g., high frequency minus the low frequency are within the transducer pass band and close to or at the resonant frequency). Where the lowest frequency is chosen to be equal to the resonant frequency, the second order intermodulation component and the sub-harmonic of the high frequency waveform are within the transducer pass band and at the resonant frequency. In the above examples, the fundamental component is considered to be cancelled out by pulse inversion. In alternative embodiments, frequencies are selected such that the intermodulation frequency or other desired frequencies are maintained while undesired frequencies at the fundamental, harmonics or other frequencies are reduced. Different frequencies are selected in alternative embodiment where the intermodulation frequency is other than the resonant frequency of the contrast agent. While the resonant frequency is given as centered at a specific frequency, the resonant frequency may be a frequency within a band of frequencies, such as where the contrast agent has a flat or broadband response.

By transmitting a waveform with pulses at two or more different frequencies, different responses are generated from tissue than from contrast agent. An intermodulation response due to the cascaded pulses from contrast agents is greater than an intermodulation response from tissue. Tissues exhibit broadband behavior so respond to frequency transitions rapidly. In general, tissues generate limited or no intermodulation signals during a single frequency transition. However, contrast agents have a slower response to a frequency transition. During the transition period, the contrast agent oscillates at both the original driving frequency as well as the new driving frequency. As a consequence, an intermodulation signal that is a function of both frequencies is generated during the transition. Response from contrast agents is different and greater than response from tissues.

In act 26, a second waveform with pulses at different frequencies is transmitted. The second waveform is transmitted sequentially after the first waveform, such as associated with transmitting a pulse of acoustic energy at a later time along a same or adjacent scan line. This subsequent firing is a repeated transmission of a first waveform or is of a different waveform. For example, pulses at different frequencies than the pulses of the first waveform are transmitted. In another embodiment, the subsequent waveform has a same number of pulses and at the same frequencies as earlier waveforms, but is transmitted at different phasing. For example, the subsequent waveform is also the waveform shown in FIG. 3 only with the initial pulse 34 starting with a negative amplitude rather than a positive amplitude or at 180 degrees out of phase with the earlier waveform. In alternative embodiments, the phasing is the same. The pulses associated with one frequency band are cascaded after pulses associated with other frequency band with no or little delay. The second subsequent waveform may be altered relative to the first or previous waveform in phasing, amplitude, aperture characteristic or other waveform characteristic, such as disclosed in any now known or later developed multi-pulse contrast agent imaging technique (see the above noted patents).

In alternative embodiments, a single pulse imaging technique is used. Intermodulation information is isolated or obtained in response to a single transmission. Act 26 is skipped, not performed or used for subsequent imaging.

Echoes responsive to the transmitted waveforms are received. The echoes include energy responsive to the tissue and any contrast agents. The echoes include information at fundamental, harmonic, sub-harmonic, intermodulation and/or other frequencies.

In act 28, information responsive to one or more of the transmissions is isolated. Information at an intermodulation frequency is isolated from other information. For example, information at an intermodulation frequency and a different frequency is isolated from information at a fundamental frequency. The intermodulation frequency is the difference between the frequencies of the pulses transmitted with the waveforms, such as responsive to a frequency transition. Isolating is used herein to indicate maintaining, increasing or reducing less than information at a different frequency but not necessarily information at all other frequencies or frequency bands. In one embodiment, information at the intermodulation frequency and any other desired frequencies is received along multiple depths of a scan line, such as receiving substantially a same frequency band along each depth. Substantially is used to account for frequency band variation due to the frequency based attenuation. In alternative embodiments, the frequency band for reception varies as a function of depth, such as to account for frequency dependent focusing. Any of various frequencies of interest may be isolated, including the intermodulation frequency, an integer harmonic frequency of a lower of the two frequency bands used for transmission, a sub-harmonic frequency band of a higher of the two or more frequency bands used for transmission and information at frequency bands showing a loss of correlation of the at least two waveforms (e.g., fundamental frequency). Any of the various frequencies of interest may have overlapping or the same frequency bands or different frequency bands. By isolating information at the intermodulation frequency from at least one other frequency, the resulting information more likely contains contrast agent response than tissue responsive information.

Any of various techniques for isolating information may be used, such as filtering using analog or digital components (e.g. transducer response, circuitry response, or FIR or IIR digital filtering). A combination of signals responsive to two different transmissions may also be used to isolate desired information. For example, signals responsive to the first waveform are combined with signals responsive to a subsequently transmitted waveform. Where the waveforms have been phase inverted relative to each other, adding the responses cancels odd harmonic information, such as information at the fundamental and third harmonics of both or all of the frequencies used in the transmit waveforms. Even harmonics, sub-harmonics and intermodulation frequency information of any or all of the frequencies of the transmit waveforms are maintained or reduced less than the fundamental frequency information. In alternative embodiments, a same phasing or different phasing is used and echoes responsive to the two different waveforms are subtracted from each other. Other functions and relative characteristics of sequential waveforms may be used for isolating information at a desired frequency band, such as adjusting both the phase and relative amplitude between different waveforms and applying different weightings and/or phasing to the receive echo signals for combination.

Due to the differences in response between tissue and contrast agent, information at an intermodulation frequency provides a larger contrast agent-to-tissue ratio. Both contrast agent and tissues have non-linear response. When an acoustic waveform propagates through the contrast agent and tissues, an intermodulation component is generated where more than one frequency component is provided in the waveform. By having a sudden step transition between two pulses with substantially different or step transitions in frequency, in intermodulation component spaced from the fundamental transmitted frequencies or at fundamental transmit frequencies is generated.

FIG. 4A shows a four cycle 2 MHz waveform transmitted by a transducer 14, such as a C5-2 transducer available from Siemens Medical Solutions USA. FIG. 4B shows the magnitude of response from tissue and contrast agents as a function of frequency to the transmit waveform of FIG. 4A. The tissue and contrast agent responses of FIG. 4B are a two-way response using phase inversion combination. The waveform of FIG. 4A is transmitted sequentially 180 degrees out of phase, the responses are equally weighted, and the responses are added. As shown in FIG. 4B, the fundamental components around the 2 MHz range is reduced or eliminated as compared to the second harmonic at 4 MHz. The tissue response is 10 to 15 dB greater than the contrast agent response.

FIG. 5A shows a transmit waveform with pulses at two different frequencies. Rather than cascading the transmit pulses without any overlap, the transmit pulses at the two different frequencies overlap throughout the entire waveform. For example, a four cycle 2 MHz waveform is provided with an overlapping 8 cycle 4 MHz waveform. FIG. 5B shows a two-way response of tissue and contrast agent to a two pulse phase inversion combination using the waveform of FIG. 5A. Due to the phase inversion, information at the fundamental frequencies is cancelled or reduced relative to information at harmonic frequencies. As shown in FIG. 5B, second harmonic information at 4 MHz generated by the 2 MHz pulses and sub-harmonic and intermodulation frequency components near 2 MHz remain. By providing pulses at multiple different frequencies, the response of the contrast agent is greater than the response at the tissue. A lower frequency band transducer may be used given the lower frequencies of the intermodulation component. Since the pulses at different frequencies are provided with complete overlap, the tissue response may include an intermodulation component.

Figure 6A:
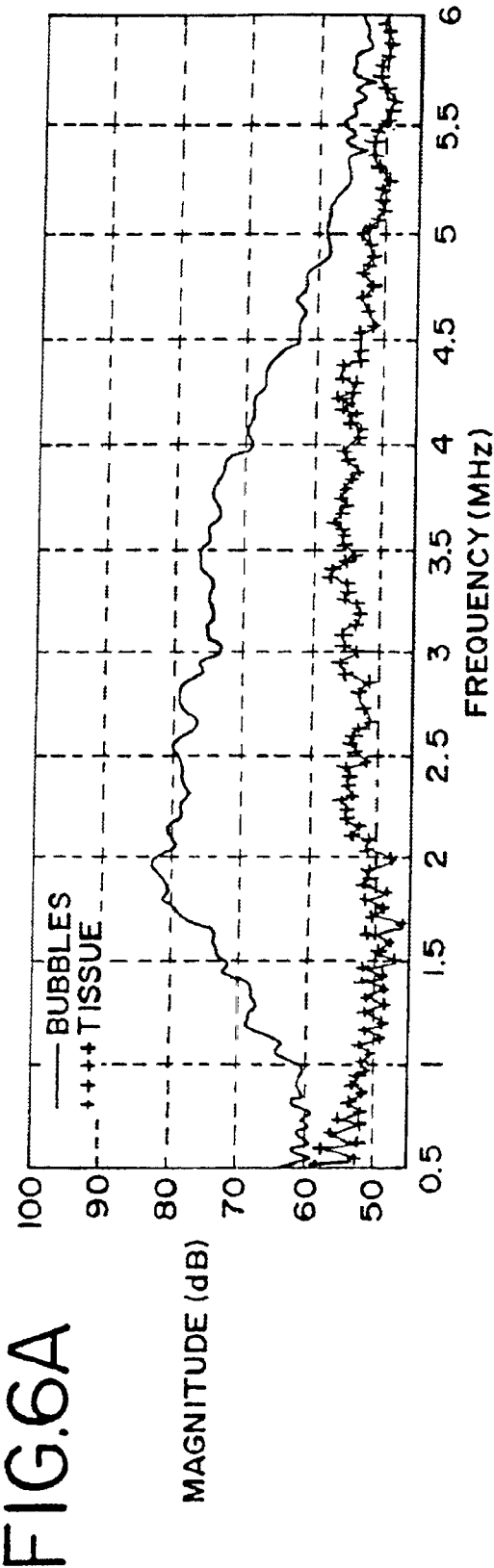
FIGS. 6A and 6B are graphical representations of tissue and contrast agent responses to sequentially transmitted waveforms with pulses at two different frequencies where the sequential waveforms are out of phase and the responses are added.
Figure 6B:
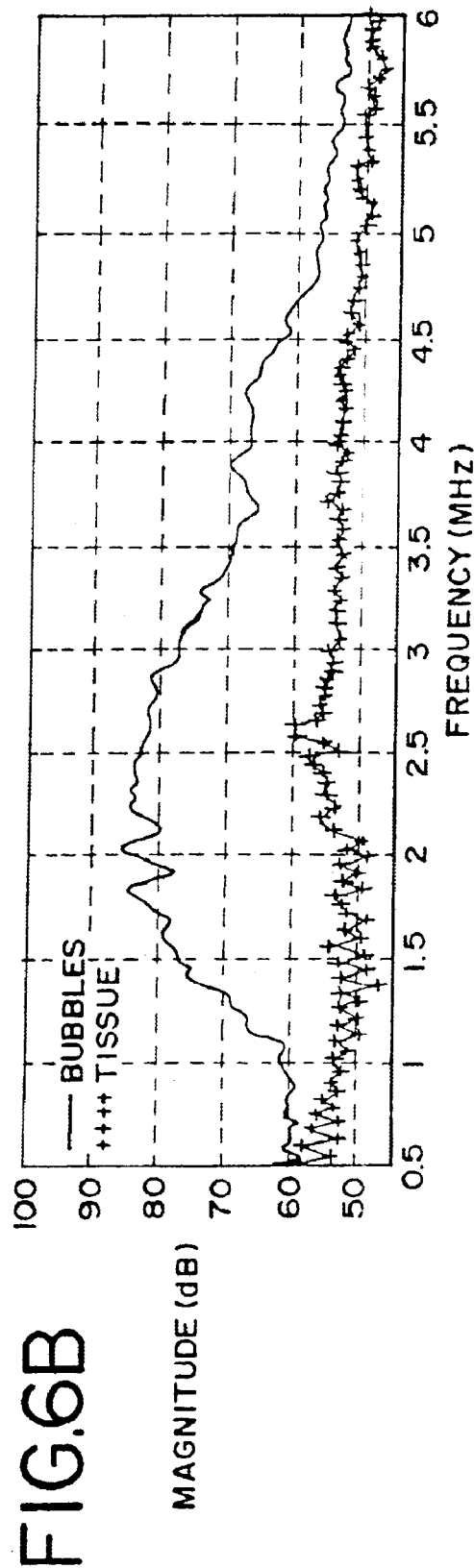

FIGS. 6A and 6b show the two way, phase inversion response using the transmit waveform shown in FIG. 3. For FIG. 6A, the transmit waveform includes pulses for one cycle at 1.25 MHz and pulses for two cycles at 3.6 MHz. For FIG. 6B, the transmit waveform includes pulses for one cycle at 2 MHz and pulses for two cycles at 4 MHz. Unlike the waveform of FIG. 5A, the pulses at different frequencies are cascaded without overlap. The transition from pulses at one frequency to pulses at another frequency is about 0 second delay. As shown in FIG. 6A, contrast agents provide a large magnitude response at the intermodulation frequency centered at about 2.35 MHz while the tissue response is greatly reduced in magnitude at the intermodulation frequency. For FIG. 6B, the contrast agent shows intermodulation and sub-harmonic frequency response at 2 MHz for contrast agent with reduced magnitude for the tissue response at the intermodulation and sub-harmonic frequencies. Given the reduced magnitude of the tissue response, the increased magnitude of the contrast agent may result from the intermodulation frequencies. While examples are provided above using waveforms of any number of cycles and frequencies, different waveforms with different numbers of cycles, frequencies, amount of overlap, or other characteristics may be provided. Different tissues and different contrast agents may provide different responses.

Cascading low frequency and high frequency pulses together in a transmit waveform allows detection of harmonic and intermodulation information as well as loss of correlation information simultaneously using phase inversion or multi-pulse techniques. Using pulses at a low frequency, such as a frequency lower than a resonant frequency of the contrast agent (e.g. 0.5 $F_0$), allows for better penetration within a patient. Low transmit frequencies may also produce weaker tissue harmonic information, further enhancing the contrast-to-tissue ratio. For example, the tissue harmonic strength, $P_2 \sim xfBP^2$, where x is the propagation distance, f is the frequency of the signal, B is a non-linear response constant or factor for the tissue, P is the strength of the fundamental signal. The second harmonic is weaker for lower transmit frequencies. For contrast agents with the second harmonic at the resonant frequency of the contrast agent, stronger second harmonic contrast agent signals are generated. Lower transmit frequencies also result in the second and third harmonic generated by contrast agents being more likely within the pass band of the transducer 14. High transmit frequencies may be more sensitive to contrast flow motion or loss of correlation between sequential pulses. In firing two or three pulses and combining the responsive receive signals, a loss of correlation due to flow, destruction or movement of the contrast agent is detected. By including pulses at low frequencies and pulses at high frequencies, both harmonic and loss of correlation information is more likely included in the received information.

Referring to FIG. 2, an image is generated. The image is responsive to the isolated information in act 30. For example, a contrast agent image is generated based on the intermodulation frequency alone or intermodulation frequencies as well as other frequency bands. As another example, isolated contrast agent information is overlaid on information responsive to tissue information or tissue and other information. Any of color or gray scale modulation of one or more components of an image may be used, such as using a gray scale representation of contrast information overlaid on a gray scale representation of the tissue of the region.

Various alternatives in addition to the alternative embodiments discussed above are possible. For example, the transmit waveform with pulses at different frequencies, such as shown in FIG. 3, is generated in the acoustic domain. Pulses at one frequency are generated at a plurality of elements that is less than an entire aperture, such as even number elements. The pulses of a different frequency are generated at other elements, such as the odd number elements. Based on relative timing between the pulses from each of the elements, the waveform shown in FIG. 3 or other waveform with pulses cascaded at different frequencies is generated in the acoustic domain. For multi-dimensional arrays, different rows may transmit different pulses with delay relative to each other for summation in the acoustic domain.

While the invention has been described above by reference to various embodiments, it should be understood that many changes and modifications can be made without departing from the scope of the invention. For example, the transmit waveform is a chirp waveform with a gradual transition between frequencies. The chirp waveform includes pulses at two or more desired frequencies (e.g. $0.5f_0$ and $2 f_0$). As another example, the frequencies of the pulses are selected such that the resonant frequency is not at the intermodulation frequency band. As yet another example, the intermodulation response is used for tissue imaging, such as described above using the overlapping pulses of FIG. 5A. Both of center frequency, frequency and frequency band have been used herein. In general, these terms are used interchangeably. The center frequency is one of the frequency with the greatest magnitude (e.g. primary frequency of an infinite square wave) or the center most frequency within a band of frequencies. A frequency band is either a range of frequencies centered about a center frequency or defined by a threshold magnitude (e.g. −6 dB or −3 dB from a peak magnitude). "Frequency" includes either a center frequency, a band of frequencies, a frequency within a band of frequencies or combinations thereof.

It is therefore intended that the foregoing detailed description be regarded as illustrative rather than limiting, and that it be understood that it is the following claims, including all equivalents, that are intended to define the spirit and scope of this invention.

I (We) claim:

1. A method for spread spectrum coding in ultrasound contrast agent imaging, the method comprising:

(a) transmitting a first waveform having pulses at first and second frequencies, the first frequency different than the second frequency, pulses at the first frequency cascaded with the pulses at the second frequency without overlap;

(b) isolating information responsive to (a) at an intermodulation frequency; and (c) generating an image responsive to the isolated information.

2. The method of claim 1 wherein (a) comprises generating a first response in tissue due to the first waveform and generating a second response in contrast agents due to the first waveform, the second response different than the first response, an intermodulation response of the second response being greater than an intermodulation response of the first response.

3. The method of claim 1 further comprising:

(d) transmitting a second waveform having pulses at third and fourth frequencies, the third frequency different than the fourth frequency;

wherein (b) comprises combining information responsive to the second waveform with information responsive to the first waveform.

4. The method of claim 1 wherein (b) comprises isolating information at the intermodulation frequency, the intermodulation frequency being responsive to a difference between the first and second frequencies.

5. The method of claim 1 further comprising:

(d) repeating (a) with the first waveform at a different phase in (a) than (d);

wherein (b) comprises adding a response to (a) with a response to (d).

6. The method of claim 1 wherein (c) comprises generating a contrast agent image.

7. The method of claim 1 wherein (a) comprises transmitting with the first waveform wherein the pulses step from the first frequency to the second frequency without a gradual transition, a difference between the first and second frequencies being greater than half the least of the first and second frequencies.

8. The method of claim 1 wherein (c) comprises generating the image responsive to isolated information and responsive to isolated tissue information.

9. In a method for ultrasound contrast agent imaging where ultrasound energy is (a) transmitted into a region with tissue and contrast agent and echoes of the energy from the tissue and contrast agent are (b) received, an improvement in (a) comprising:

(a1) transmitting at least two waveforms sequentially into the region, each of the at least two waveforms having pulses at two or more different frequencies, the pulses at two or more different frequencies cascaded with a step transition between frequencies.

10. The improvement of claim 9 wherein (a1) comprises:

(a1a) transmitting a first waveform having at least one first pulse at a first frequency and at least one second pulse at a second frequency different than the first frequency, the first pulse cascaded with the second pulse in a stepped transition from the first frequency to the second frequencies; and (a1b) transmitting a second waveform having at least one third pulse at a third frequency and at least one fourth pulse at a fourth frequency different than the third frequency, the third pulse cascaded with the fourth pulse in a stepped transition from the third to the fourth frequencies.

11. The improvement of claim 9 wherein (a1) comprises transmitting with the pulses at two or more different frequencies cascaded with the step transition between frequencies, the pulses of each frequency being sequential without overlap.

12. The improvement of claim 9 wherein (a1) comprises transmitting with the pulses of each waveform at two or more different frequencies cascaded with step transition between frequencies being without a gradual transition, a difference between the two different frequencies being greater than half the least of the two different frequencies.

13. The improvement of claim 9 wherein (a1) comprises transmitting each waveform with pulses at a first frequency $f_1$ and pulses at a second frequency $f_2$, a difference between the $f_1$ and $f_2$ being substantially a resonant frequency $f_0$ of contrast agents.

14. The improvement of claim 10 wherein the first frequency is substantially the same as the third frequency and the second frequency is substantially the same as the fourth frequency.

15. The improvement of claim 9 wherein (a1) comprises transmitting the at least two waveforms at different phases;

wherein (b) comprises adding a response to a first of the at least two waveforms with a response to a second of the at least two waveforms.

16. The improvement of claim 9 wherein (b) comprises isolating information at an intermodulation frequency of the two different frequencies.

17. The improvement of claim 9 wherein (a1) comprises transmitting with both a first and second of the two different frequencies focused at a first point, wherein (b) comprises receiving at a substantially same frequency band along multiple depths of a scan line in response to (a1).

18. The improvement of claim 9 wherein (a1) comprises transmitting wherein the pulses of each waveform consist of pulses at only two primary frequencies.

19. The improvement of claim 9 wherein (a1) comprises transmitting the pulses at a first of the two different frequencies from a first plurality of elements and transmitting the pulses at second of the two different frequencies from a second plurality of elements, the second plurality of elements being different than the first plurality of elements, the waveforms combining in the acoustic domain in response to the transmissions having the cascaded pulses.

20. The improvement of claim 9 wherein (b) comprises isolating information of at least two of: an integer harmonic frequency of a lower of the at least two different frequencies, a sub-harmonic frequency of a higher of the at least two different frequencies, an intermodulation frequency of the at least two different frequencies, and a loss-of-correlation of the at least two waveforms.

21. The improvement of claim 9 wherein (a1) comprises transmitting one of the at least two waveforms from a plurality of elements substantially simultaneously, at least one of amplitude and phase of pulses at a first frequency of the two or more different frequencies being different than a corresponding one of amplitude and phase of pulses at a second frequency of the two or more different frequencies.

22. The improvement of claim 21 further comprising:

(c) setting the at least one of amplitude and phase of pulses at the first frequency relative to the corresponding one of amplitude and phase of pulses at the second frequency such that acoustic energy is more evenly distributed along a scan line than setting the amplitudes and phases the same.

23. The improvement of claim 9 wherein (a1) comprises transmitting pulses with an energy responsive to pulse width modulation.

* * * * *